US012642927B2

(12) United States Patent
Schregel

(10) Patent No.: US 12,642,927 B2
(45) Date of Patent: Jun. 2, 2026

(54) COUPLING BETWEEN DRIVE AND BLOWER HEAD

(71) Applicant: Loewenstein Medical Technology S.A., Luxembourg (LU)

(72) Inventor: Christian-Georg Schregel, Friedberg (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 870 days.

(21) Appl. No.: 18/046,188

(22) Filed: Oct. 13, 2022

(65) Prior Publication Data

US 2023/0120694 A1 Apr. 20, 2023

(30) Foreign Application Priority Data

Oct. 16, 2021 (DE) .......................... 102021005180.7

(51) Int. Cl.
| | |
|---|---|
| *A61M 16/00* | (2006.01) |
| *A61M 16/01* | (2006.01) |
| *A61M 16/10* | (2006.01) |
| *A61M 16/12* | (2006.01) |

(52) U.S. Cl.
CPC .......... *A61M 16/0066* (2013.01); *A61M 16/01* (2013.01); *A61M 16/104* (2013.01); *A61M 16/125* (2014.02); *A61M 2205/121* (2013.01); *A61M 2207/00* (2013.01)

(58) Field of Classification Search
CPC .......... A61M 16/0057; A61M 16/0066; A61M 16/01; A61M 16/104; A61M 16/125; A61M 2205/0272; A61M 2205/121; F04D 13/022; F04D 13/024; F04D 13/025; F04D 29/058; F04D 29/601; F04D 29/603; F04D 25/0606; H02N 15/00; A62B 18/006; A62B 18/045
See application file for complete search history.

(56) References Cited

U.S. PATENT DOCUMENTS

| | | | | |
|---|---|---|---|---|
| 6,526,970 | B2 | 3/2003 | Devries et al. | |
| 6,672,300 | B1 * | 1/2004 | Grant .................. | A61M 16/205 |
| | | | | 128/204.22 |
| 2002/0000228 | A1 * | 1/2002 | Schoeb ................ | F16C 32/044 |
| | | | | 128/204.19 |
| 2010/0000535 | A1 * | 1/2010 | Wickham .............. | A61M 16/20 |
| | | | | 128/205.24 |
| 2011/0288428 | A1 * | 11/2011 | Valentine .............. | A61B 5/097 |
| | | | | 128/205.12 |

(Continued)

FOREIGN PATENT DOCUMENTS

| | | | | |
|---|---|---|---|---|
| CN | 110645192 A | * | 1/2020 | ........... F04D 25/082 |
| DE | 20022295 U1 | | 8/2001 | |
| EP | 1170025 A1 | | 8/2005 | |

OTHER PUBLICATIONS

Machine translation of CN-110645192-A.*

*Primary Examiner* — Joseph D. Boecker

(74) *Attorney, Agent, or Firm* — Abel Schillinger, LLP

(57) ABSTRACT

A ventilator having a blower head comprising at least one fan wheel and a housing having blower nozzles, as well as a drive device. The blower head together with the drive device is configured to convey a patient gas and the blower head and the drive device are detachably coupled to one another via a coupling.

12 Claims, 5 Drawing Sheets

(56)                  References Cited

U.S. PATENT DOCUMENTS

| | | | |
|---|---|---|---|
| 2014/0005566 A1 | 1/2014 | Homuth et al. | |
| 2014/0020684 A1* | 1/2014 | Klasek .................. | A61M 16/16 |
| | | | 128/203.26 |
| 2014/0234141 A1* | 8/2014 | Hoshi ..................... | F04D 13/02 |
| | | | 417/420 |
| 2018/0104436 A1 | 4/2018 | Leonard et al. | |
| 2023/0136168 A1* | 5/2023 | Castellote .............. | F04D 25/06 |
| | | | 417/423.14 |

\* cited by examiner

US 12,642,927 B2

US 12,642,927 B2

US 12,642,927 B2

US 12,642,927 B2

1

COUPLING BETWEEN DRIVE AND BLOWER HEAD

CROSS-REFERENCE TO RELATED APPLICATIONS

The present application claims priority under 35 U.S.C. § 119 of German Patent Application No. 102021005180.7, filed Oct. 16, 2021, the entire disclosure of which is expressly incorporated by reference herein.

BACKGROUND OF THE INVENTION

1. Field of the Invention

The invention relates to a coupling between a motor and a blower head and to a ventilator having said coupling.

2. Discussion of Background Information

Ventilators used especially in the clinical setting require regular hygienic treatment. Said hygienic treatment concerns especially the parts of the ventilator that convey and conduct the patient gas. In some ventilators, contact with the patient gas is made by, inter alia, the blower. Generally, the blower is directly connected to the motor, meaning that the motor is also considered to be contaminated with patient gas. In the prior art, it is known that the entire element comprising motor and blower can be removed from the ventilator for treatment. As a result, the motor must be designed for hygienic treatment, for example through robust bearings and appropriate electronic components. Despite the specially selected materials and components, a greatly reduced service life of the motor can nevertheless be assumed.

In view of the foregoing, it would be advantageous to have available a coupling between motor and blower, so that the motor and the blower can be treated separately.

SUMMARY OF THE INVENTION

The invention provides a ventilator having a blower head which comprises at least one fan wheel and a housing having blower nozzles, and a drive device. The blower head together with the drive device is configured to convey a patient gas and the blower head and the drive device are detachably coupled to one another via a coupling.

In some embodiments, the ventilator is characterized in that the coupling is arranged and configured such that, in the region of the coupling, no patient gas reaches the drive device from the blower head.

In some embodiments, the ventilator is characterized in that the coupling is a force-locking connection and/or an interlocking connection.

In some embodiments, the ventilator is characterized in that the coupling between the drive device and the blower head is effected via at least two coupling elements.

In some embodiments, the ventilator is characterized in that the drive device has a motor shaft, wherein at least one first coupling element is arranged on the motor shaft.

In some embodiments, the ventilator is characterized in that at least one second coupling element is arranged on the fan wheel and/or in that the fan wheel is connected to a fan shaft, wherein at least one second coupling element is arranged on the fan shaft.

In some embodiments, the ventilator is characterized in that the coupling is a magnetic coupling.

In some embodiments, the ventilator is characterized in that the coupling is a magnetic connection.

In some embodiments, the ventilator is characterized in that the at least two coupling elements are in the form of at least two coupling magnets.

In some embodiments, the ventilator is characterized in that at least one first coupling magnet is arranged on the fan wheel and in that at least one second coupling magnet is arranged on the motor shaft.

In some embodiments, the ventilator is characterized in that the coupling elements are arranged and configured to form a magnetic connection with one another.

In some embodiments, the ventilator is characterized in that the housing of the blower head is at least partially arranged between the coupling magnet of the fan wheel and the coupling magnet of the motor shaft.

In some embodiments, the ventilator is characterized in that the blower head and/or the blower part is/are in the form of a wearing part.

In some embodiments, the ventilator is characterized in that the blower head and/or the blower part is/are in the form of a treatment part and is/are designed for treatment in a thermal disinfector and/or an autoclave.

In some embodiments, the ventilator is characterized in that the coupling is a force-locking connection.

In some embodiments, the ventilator is characterized in that the coupling between drive device and blower head is effected via a friction fit.

In some embodiments, the ventilator is characterized in that the coupling is an interlocking connection, wherein the coupling elements have a symmetric coupling profile.

In some embodiments, the ventilator is characterized in that the coupling is an interlocking connection.

In some embodiments, the ventilator is characterized in that the coupling elements have an asymmetric coupling profile.

In some embodiments, the ventilator is characterized in that the drive device is fixedly installed in the ventilator.

In some embodiments, the ventilator is characterized in that the blower part and/or the gas pass part is/are designed for treatment in a thermal disinfector and/or autoclave.

The invention also provides a blower head, comprising at least one fan wheel and one housing having blower nozzles. The blower head is couplable to a drive device of a ventilator according to the invention via a detachable coupling.

The invention also provides a method for coupling a blower head which comprises at least one fan wheel and one housing having blower nozzles to a drive device of a ventilator, where the coupling is detachable.

It is to be noted that the features presented individually in the claims can be combined with one another in any technically meaningful way and they indicate further embodiments of the invention. The description provides additional characterization and specification of the invention, especially in connection with the drawings.

It should be further noted that an "and/or" conjunction that is used herein and that is between two features and links them together is always to be interpreted as meaning that only the first feature can be present in a first embodiment of the subject matter according to the invention, only the second feature can be present in a second embodiment, and both the first and the second feature can be present in a third embodiment.

A ventilator is to be understood to mean any device which assists a user or patient with natural respiration, undertakes the ventilation of the user or living being (e.g., patient and/or newborn and/or premature baby) and/or is used for respiratory therapy and/or influences the respiration of the user or patient in another way. Non-exhaustive examples thereof include CPAP and BiLevel machines, anesthetic machines, respiratory therapy devices, (clinical, outpatient or emergency) ventilators, high-flow therapy devices, and cough machines. Ventilators can also be understood to mean diagnostic devices for ventilation. Said diagnostic devices can generally be used to measure medical and/or respiration-based parameters of a living being. These also include devices which can measure and optionally process medical parameters of patients in combination with respiration or only in relation to respiration.

Unless expressly described otherwise, a patient interface can be understood to mean any peripheral device intended for interaction of the measurement device with a living being, especially for therapeutic or diagnostic purposes. In particular, a patient interface can be understood to mean a mask of a ventilator or a mask connected to the ventilator. Said mask can be a full-face mask, i.e., a mask surrounding the nose and mouth, or a nasal mask, i.e., a mask only surrounding the nose. Tracheal tubes or cannulas and so-called nasal cannulas can be used as a mask or patient interface, too. In some cases, the patient interface can also be a simple mouthpiece, for example a tube, through which the living being at least exhales and/or inhales.

According to the invention, the blower head is air-tightly separated from the drive device in the region of the coupling. Depending on the type of coupling, no through-hole for a bearing and/or a shaft connected to the fan wheel (also referred to as impeller or wheel) is provided through the housing of the blower head or the corresponding blower part. The blower head is, for example, removable from the ventilator independently of the drive device and can be treated separately and/or be exchanged. Patient gas cannot reach the drive device from the blower part, at least in the region of the coupling between drive device and fan wheel.

Owing to the respiratory gas pass, the respiratory gas or the patient gas is conducted at least within the ventilator. The entire respiratory gas pass can be divided into multiple parts which can be removed from the ventilator, optionally independently of one another. The drive device by contrast can, for example, remain fixedly mounted in the ventilator and need not be hygienically treated. The selection of available components and materials for the drive device can thus be broadened. In some embodiments, it is also possible that the drive device can likewise be removed separately (independently of blower head and/or other components).

The coupling between drive device and blower head is, for example, effected magnetically. To this end, a coupling magnet is applied to the motor shaft driven by the drive device and a corresponding coupling magnet is likewise arranged on the fan wheel. The fan wheel is rotatably mounted in the blower head. Running between the coupling magnet of the fan wheel and the coupling magnet of the motor shaft, without any breach/through-hole, is the housing of the blower head or the blower part. Power transmission from the drive device to the fan wheel is effected by the magnetic field of the coupling magnets.

This complete separation of drive device and blower head that is thus possible allows construction of the blower head and components of the blower head purely from treatment-suitable materials such as PA (polyamide), PEEK (polyetheretherketone), ceramic and stainless steel.

The omission of the drive device as component to be treated or autoclavable component means that the construction of the blower part can be better adapted for the utilization of the available space in thermal disinfectors and autoclaves. Since there is no need to take into account a cylinder for the drive device, the circular part can, for example, be shaped purely as planar, rectangular elements, none of the edges of which exceed the dimensions of one sterilization unit (1 STU) and which are designed for a compact arrangement during treatment.

The blower head can be of a wearing design for short-term use in order to provide the customer with cost-effective disposable articles if said customer does not wish to perform any treatment, or the blower head can be designed for a long service life with multiple treatments. Both variants can be used with the same drive device, meaning that the customer always has the choice.

In addition, changing the shape of the housing of the blower head and of the fan wheel can influence the performance characteristics of the blower. As a result, the user has the option of changing the performance data by simply exchanging the circular part. In addition, it is also possible that the ventilator automatically detects, for example electronically detects, the variant of the blower head that is used.

The inventive coupling is, for example, part of a ventilator. In particular, the ventilator can be an intensive-care ventilator, a clinical ventilator and/or an anesthetic machine. In some embodiments, the patient gas is at least partially guided in a loop. The patient inhales via an inspiration branch and exhales into an expiration branch. The exhaled patient gas is, for example, guided through the ventilator such that it—with or without treatment (admixing with fresh oxygen, filtering to remove $CO_2$, etc.)—can be re-inhaled by the patient. For example, the blower, at least comprising a blower head having a fan wheel and a drive device for the fan wheel, ensures circulation or conveyance of the patient gas in the loop.

The ventilator is arranged and configured to convey a respiratory gas, also patient gas, from and/or to a patient. To this end, the ventilator comprises appropriate gas passes, for example arranged in one or more gas pass parts, and also an inspiration port and an expiration port. Moreover, the ventilator comprises at least one controllable respiratory gas source, for example a blower. The blower comprises at least one blower head having a housing and a fan wheel mounted in the housing. Alternatively or additionally, the fan wheel can also be mounted in the housing wall of the housing via a fan shaft. The blower further comprises at least one drive device having a motor shaft. The drive device is, for example, a motor, for instance an electric motor. The blower head is, for example, arranged separately from the drive device in a blower part. The ventilator is controlled by a control unit. The control unit is, inter alia, arranged to control the blower. In some embodiments, the ventilator is arranged to guide the patient gas in a loop, wherein the connected patient is part of the loop. Arranged in the gas pass part or connected to the gas pass part are valves, gas mixers, $CO_2$ absorbers, etc. In some embodiments, the ventilator is an anesthetic machine. If the ventilator is an anesthetic machine, devices for adding anesthetics to the respiratory gas or patient gas are also connected to the ventilator and/or arranged in the ventilator.

The ventilator has at least one part which is removable. In some embodiments, at least two parts, a blower part and a gas pass part, are removable. The blower part comprises at least one blower head, which in turn comprises at least one fan wheel, which is arranged inside a housing. The housing has at least two blower nozzles, via which the blower part or the blower head can be gas-conductingly connected to the gas pass part. The gas pass part forms, for example, the connection between blower head and the inspiration branch and the expiration branch, for example via internal gas passes. The gas passes can comprise further elements such as valves and connections, for instance to a $CO_2$ absorber. The blower part and the gas pass part are designed such that they can be removed separately. In this way, separate hygienic treatment is, for example, possible.

For example, the drive device, for example a motor, is fixedly installed in the ventilator. Power transmission between the drive device and the fan wheel is, for example, effected via a force-locking and/or interlocking connection. For example, power transmission is effected via a magnetic coupling, with at least one coupling magnet being arranged on the fan wheel and at least one coupling magnet being arranged on a motor shaft of the drive device. Owing to the magnetic coupling, it is possible for the housing wall of the blower head or the blower part to run between the fan wheel and the motor or the drive device without the need for a breach and/or a through-hole. What can thus be achieved, for example, is that no patient gas reaches the motor or the drive device in the region of the coupling. In some embodiments, an air-tight seal is achieved here.

Alternatively or additionally, the coupling of drive device and filter wheel can be achieved via a detachable interlocking and/or force-locking connection. For example, to this end, the fan wheel also has a shaft (fan shaft), and arranged both on the motor shaft and on the fan shaft are coupling elements, via which the two shafts are coupled to one another. For example, one possibility is a force-locking connection, for instance via a friction fit. In order to achieve such a force-locking connection, the blower part is, for example, detachably fixed in the ventilator, so that power transmission from motor shaft to fan shaft can take place via the coupling elements. Alternatively or additionally, a detachable interlocking connection between motor and fan wheel can also be provided. It is possible for the coupling to be effected via symmetric or asymmetric coupling elements.

In the case of coupling between drive device and fan wheel via a friction-fit connection (friction fit) and/or interlocking connection, the fan shaft must protrude through the housing of the blower part. In order to prevent contamination of the drive device or the motor with patient gas, the fan shaft is rotatably and air-tightly mounted in the housing wall of the blower part.

It is possible that a plurality of different blower parts, differing for example in the type of blower head, can be provided and be installed in the ventilator. For example, the coupling is designed such that each of the plurality of blower parts is connectable to the drive device without having to exchange the drive device or the motor. In some embodiments, the ventilator is arranged and configured to detect which blower part and/or which blower head is installed. For example, it is possible that an RFID chip or the like is arranged in or on the blower part, via which the ventilator can perform automatic detection of the blower part. In some embodiments, it is possible that detection of the blower part or the blower head can be achieved via an electrical connection cable. Alternatively or additionally, it is possible that the blower part is provided with a barcode and/or QR code which can be scanned, optionally automatically, via the ventilator.

BRIEF DESCRIPTION OF THE DRAWINGS

Further advantages and features of the present invention will become clear from the description of the illustrative embodiments, which are explained below with reference to the accompanying drawings. In the drawings,

6

Figure 1:
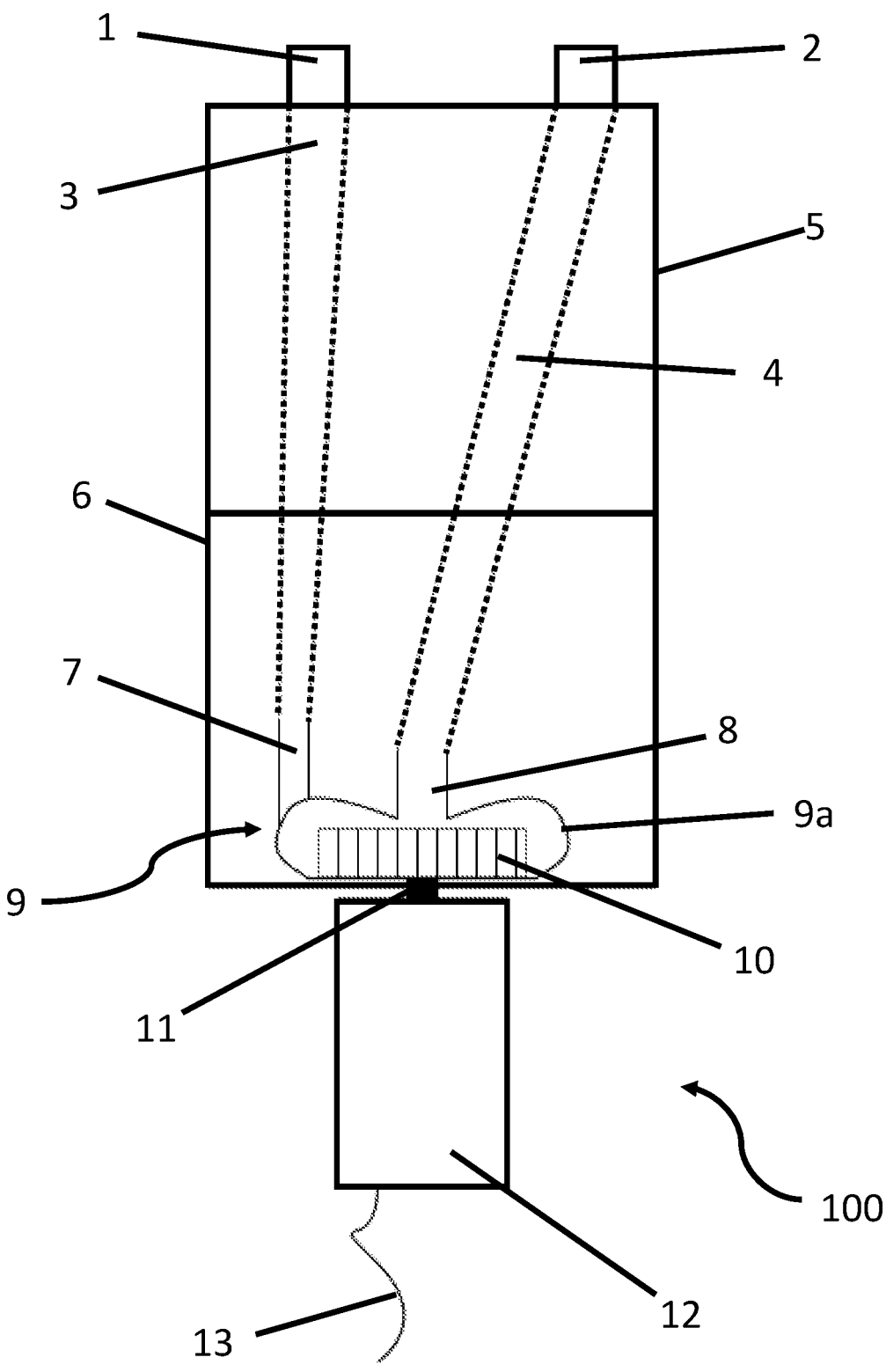
Figure 2:
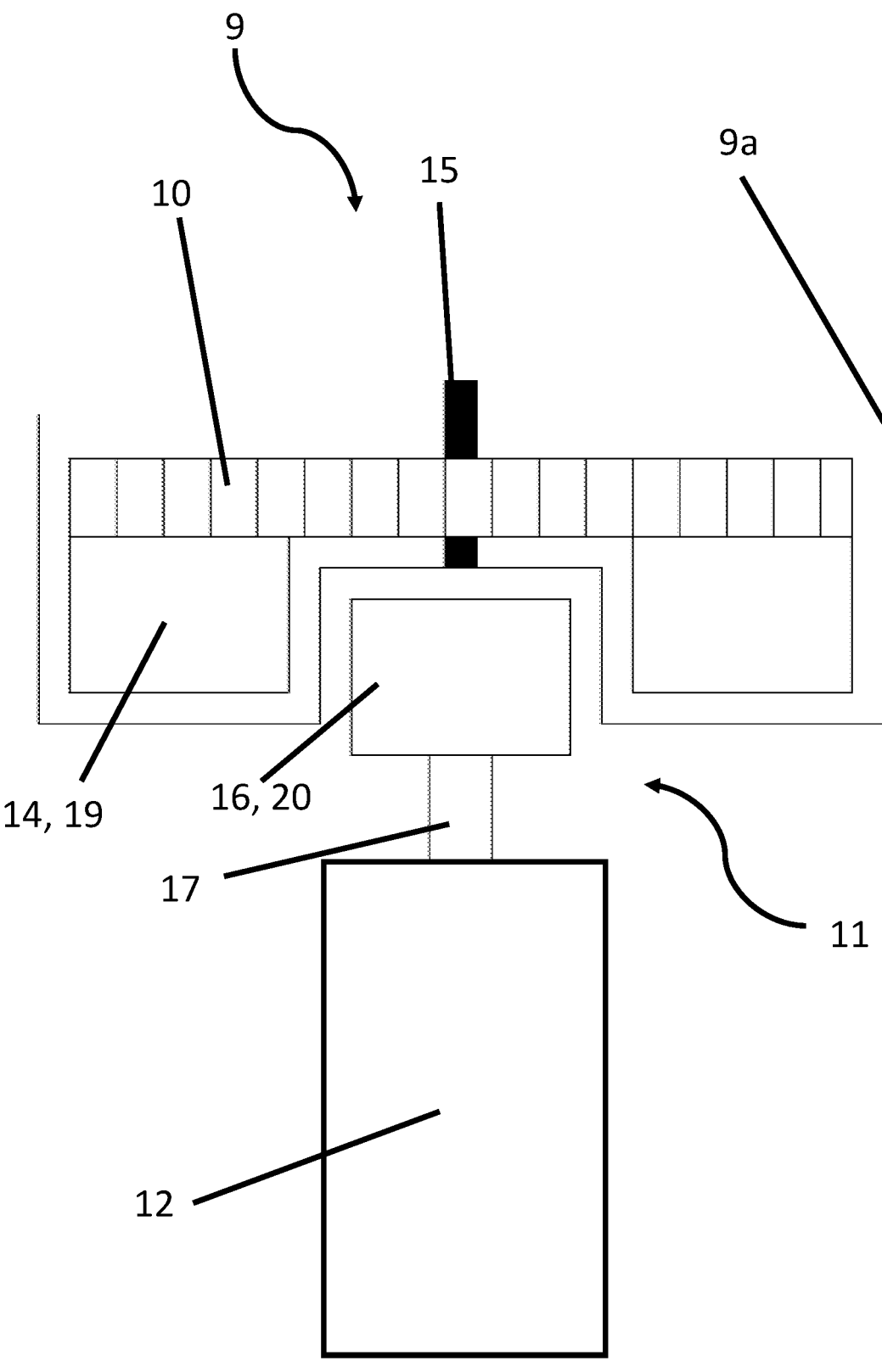
Figure 3:
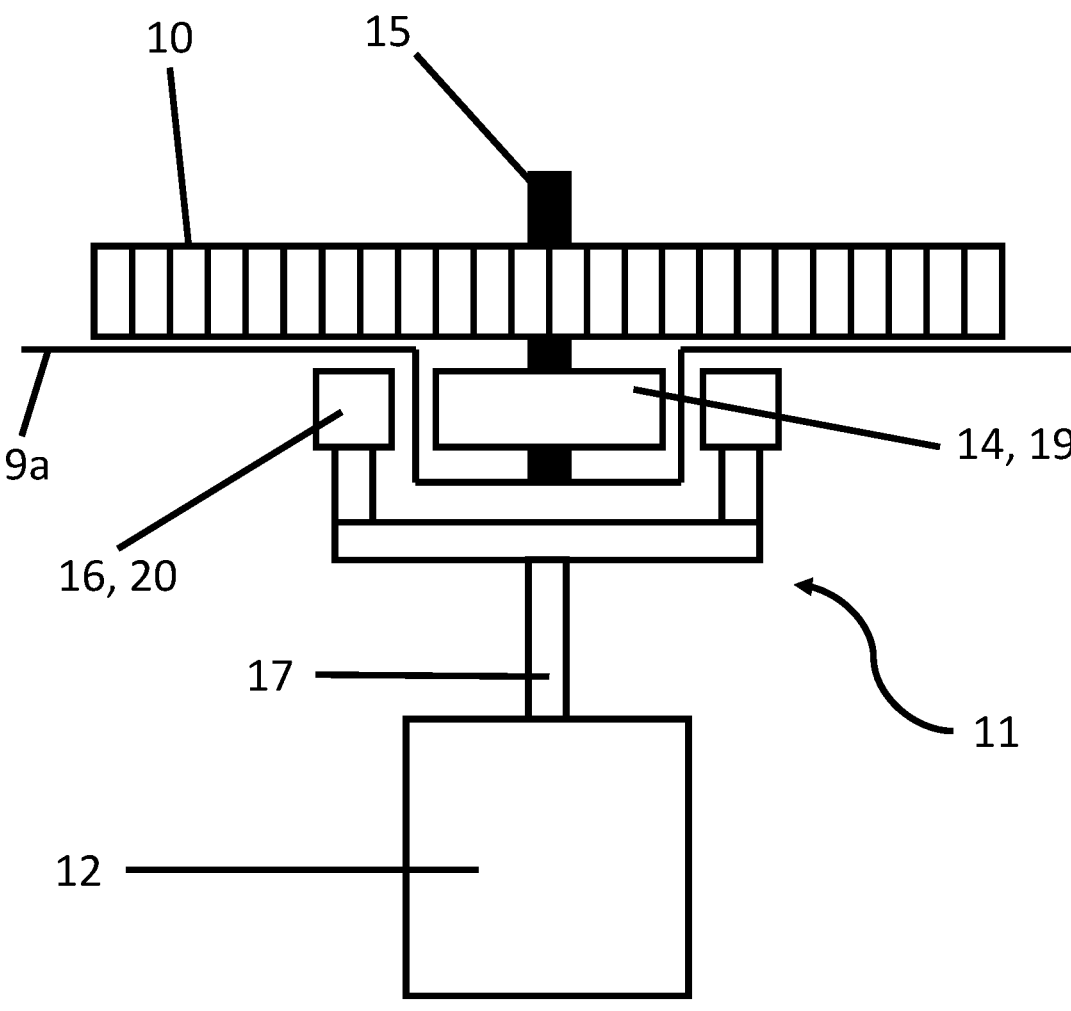
Figure 4:
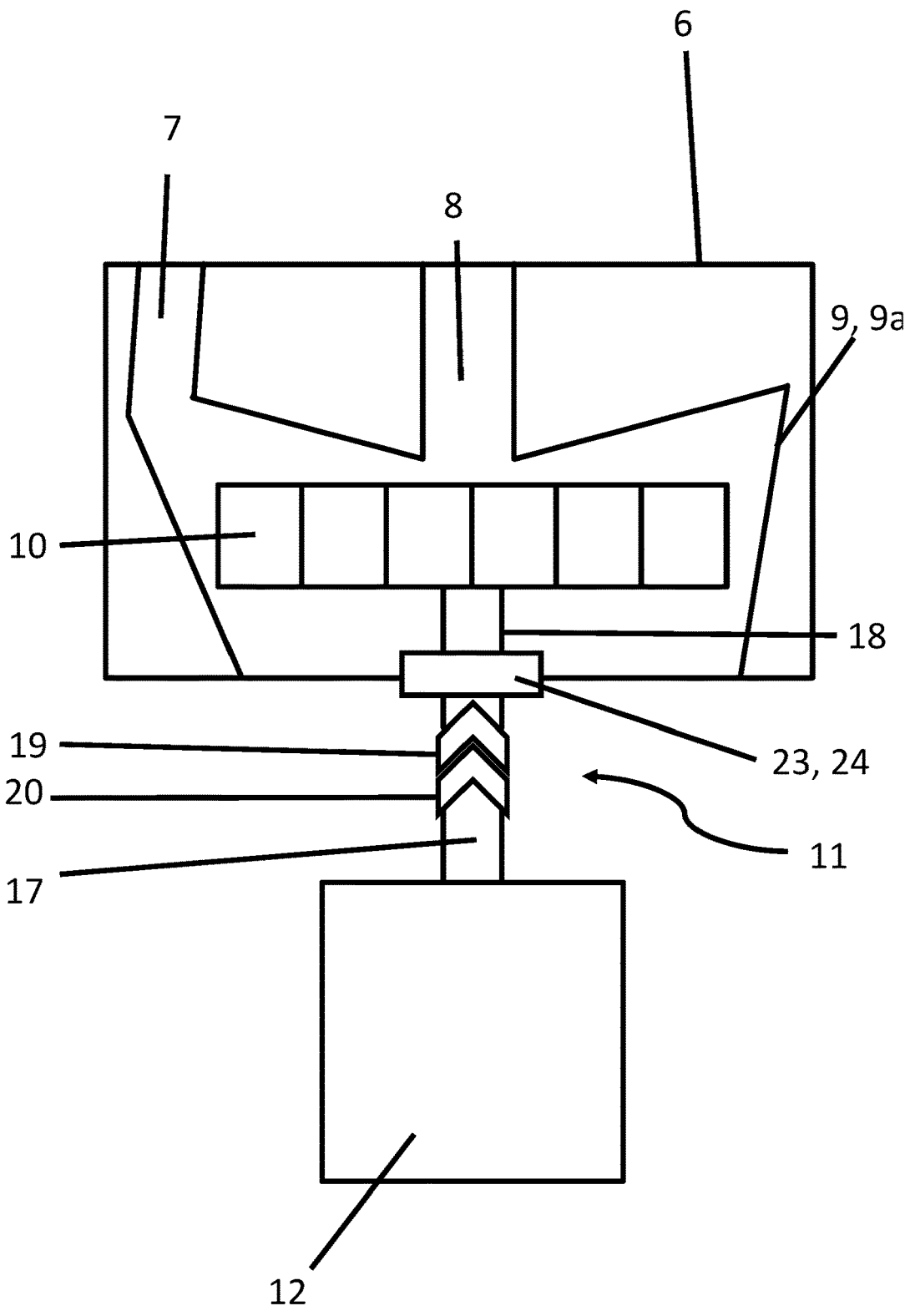
Figure 5:
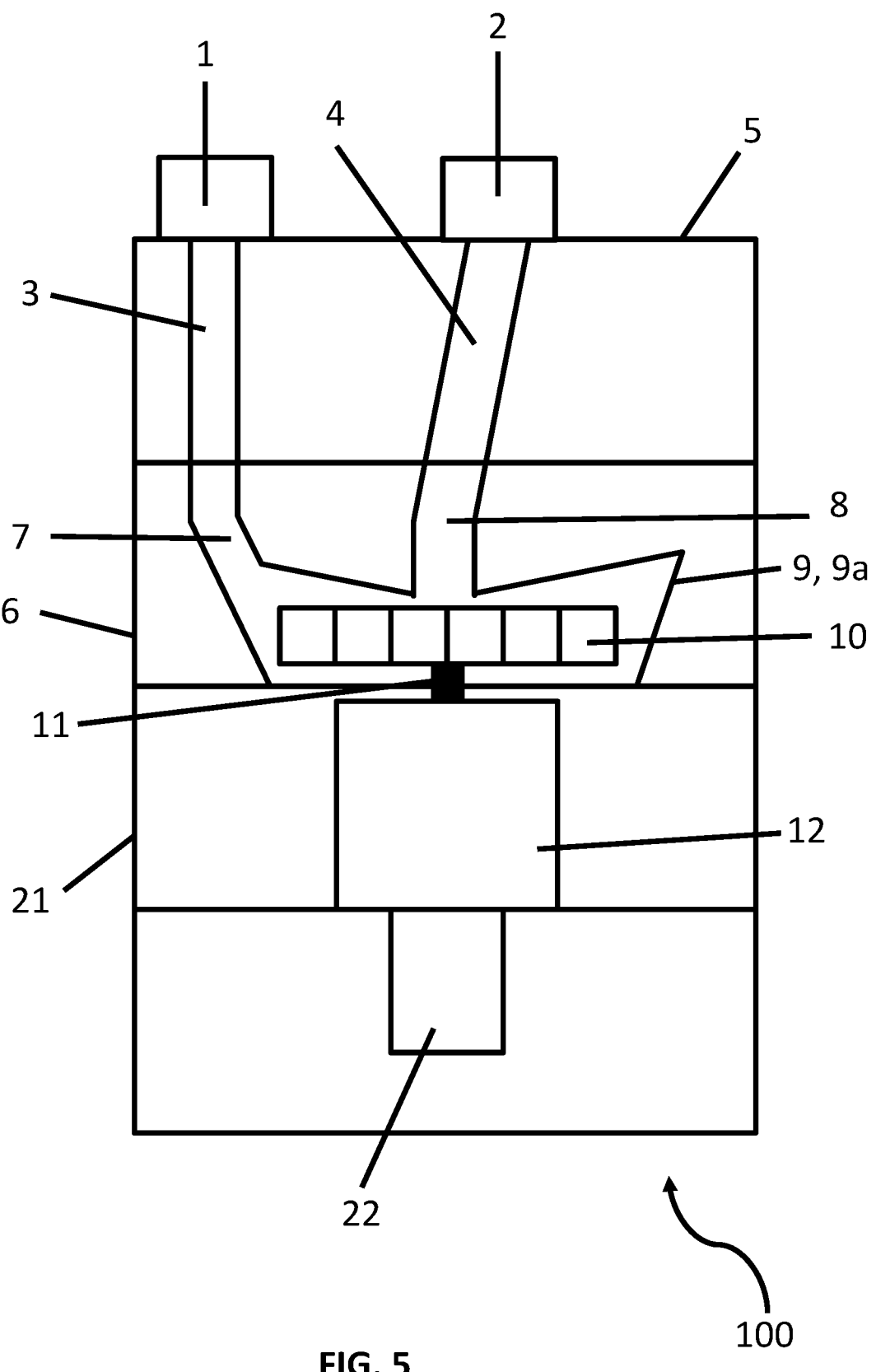

FIG. 1 shows schematically an exemplary detail of a ventilator having the coupling according to the invention and removable gas pass part and removable blower part;

FIG. 2 shows a schematic detailed view of an exemplary embodiment of the coupling;

FIG. 3 shows an exemplary embodiment of a magnetic coupling;

FIG. 4 schematically depicts an exemplary embodiment of a force-locking and/or interlocking connection as detachable coupling; and FIG. 5 schematically depicts a detail of an example ventilator.

DETAILED DESCRIPTION OF EXEMPLARY
EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

An exemplary detail of a ventilator 100 having the inventive coupling 11 and removable gas pass part 5 and removable blower part 6 is shown schematically in FIG. 1.

The gas path through the ventilator 100 is provided by the gas pass part 5 and the blower part 6. The patient gas exhaled by the patient reaches the gas pass 3 in the gas pass part 5 through the expiration branch 1. The gas pass 3 comprises, by way of example, valves and at least one connection and/or pass through a $CO_2$ absorber for removal of $CO_2$ from the exhaled patient gas. The patient gas reaches the blower part 6, which comprises at least the blower head 9, through the gas pass 3. The gas pass 3 is connected to the blower head 9 via the blower nozzle 7. The blower head 9 comprises at least one fan wheel 10, which is mounted in a bearing in the housing 9a of the blower head 9.

The fan wheel 10 is driven via a drive device, for example using a motor. Power transmission from the drive device 12 to the fan wheel 10 is effected via the coupling 11. By means of the blower, consisting of drive device and blower head 9, the patient gas is conveyed through the blower nozzle 8 into the gas pass 4 and toward the inspiration branch 2. The patient gas reaches the patient through the inspiration branch 2. The gas pass 4 comprises, for example, further valves and at least one APL valve. In addition, connections and devices can be arranged on or in the gas pass 4, by means of which gases, for example oxygen, can be added to the patient gas. If the ventilator 100 is in the form of an anesthetic machine, anesthetics can also be added to the patient gas.

By way of example, both the gas pass part 5 and the blower part 6 can be removed separately from the ventilator 100. In some embodiments, it is also possible for the gas pass part 5 to be divided into multiple individual parts which can be removed from the ventilator 100 independently of one another. For example, a modular structure of the gas pass in the ventilator 100 is thus possible.

In addition, the blower part 6 can be removed independently of the gas pass part 5 and/or the motor or drive device 12. The blower part 6 comprises at least the blower head 9 having the fan wheel 10. So that the blower head 9 can be separated from the drive device 12 or the motor, there is provided a detachable coupling 11 between drive device 12 and blower head 9. Power from the drive device 12 is transmitted to the fan wheel 10 via the detachable coupling 11. A magnetic coupling, a force-locking connection and/or an interlocking connection between drive device 12 and fan wheel 10 can be provided for the coupling 11. In particular, the coupling 11 is arranged and configured such that patient gas does not reach the drive device 12 from the blower part 6, especially the blower head 9. In some embodiments, such crossing of patient gas from the blower head 9 to the drive device 12 can take place at least not via the coupling 11.

The drive device 12 is, by way of example, supplied with energy via an electrical connection 13.

FIG. 2 shows a schematic detailed view of one exemplary embodiment of the coupling 11. The exemplary embodiment shown is a magnetic coupling, a type of force-locking connection, between drive device 12 and fan wheel 10. The coupling magnets 14, 16 are used here as coupling elements 19, 20. To this end, a coupling magnet 16 is arranged on the motor shaft 17 directly connected to the drive device 12. As a complement to the coupling magnet 16 of the motor shaft 17, at least one coupling magnet 14 is arranged on the fan wheel 10. The coupling magnets 14, 16 are, for example, permanent magnets.

The fan wheel 10 is rotatably mounted in the housing of the blower head 9 via a bearing 15. Power transmission from the drive device 12 to the fan wheel 10 is effected magnetically via the coupling magnets 14, 16. In some embodiments, there is arranged in the blower head 9 a stationary shaft on which the fan wheel 10 is rotatably mounted. For example, simple mounting can be achieved via a ball bearing. In some embodiments, the bearing 15 can be arranged in the housing wall and a shaft can establish the connection between bearing and fan wheel 10.

The exemplary coupling is assembled such that the coupling magnet 14 of the fan wheel 10 is arranged around the coupling magnet 16 of the motor shaft 17. For example, the coupling magnet 14 of the fan wheel 10 is in the form of a hollow cylinder arranged around the coupling magnet 16 of the motor shaft 17. In some embodiments, it is also possible for multiple individual coupling magnets 14 arranged at regular intervals to be arranged on the fan wheel 10. The magnetic coupling means that there is no need for material contact between motor shaft 17 and the fan wheel 10 and/or a bearing and/or a fan shaft. The possibility of patient gas reaching the motor or the drive device 12 from the blower head 9 in the region of the coupling 11 is prevented by, for example, the fact that the housing of the blower head 9 runs without any breach or other opening between drive device 12 (having a motor shaft 17 and coupling magnet 16) and the fan wheel 10 (including bearing 15, etc.). In some embodiments, the coupling 11 is air-tight.

As can be seen in FIG. 2, it is possible that the housing of the blower head 9, thus also the blower part 6, has an appropriate recess and/or indentation into which at least the coupling magnet 16 of the motor shaft 17 can be at least partially inserted. The housing wall of the blower head 9 runs between both coupling magnets 14, 16 and air-tightly separates the drive device 12 and the fan wheel 10 from one another at least in the region of the coupling 11.

Owing to the magnetic coupling 11, what can be achieved is a clear separation between a region which is not to be contaminated with patient gas and a region which is contaminated with patient gas, in which no patient gas reaches the noncontaminated region from the contaminated region. The region which is not to be contaminated comprises, for example, the drive device 12, whereas the contaminated region comprises the fan wheel 10.

The inertia of the fan wheel 10 can, inter alia, be set by the size of the coupling magnet(s) 14 used. The positioning along the radius of the wheel can also be critical as regards the inertia of the fan wheel 10.

FIG. 3 shows one exemplary embodiment of a magnetic coupling 11, in which the coupling magnet 16 of the motor shaft 17 is arranged around the coupling magnet 14 of the fan wheel 10. The coupling magnet 14 of the fan wheel 10 thus lies inside the coupling magnet 16 of the motor shaft 17. The fan wheel 10 is, by way of example, rotatably mounted via the bearing 15. Owing to the coupling magnets 14, 16, rotation of the motor shaft 17 is transmitted to the bearing 15 and/or directly to the fan wheel 10. The coupling magnet 16 of the motor shaft is, by way of example, in the form of a hollow cylinder. Alternatively or additionally, the coupling magnet 16 can also consist of a plurality of coupling magnets arranged regularly around the coupling magnet 14 of the fan wheel 10.

The blower head 9 and the blower part 6 containing the blower head 9 have, by way of example, a bulge which can be surrounded by the coupling magnet 16 of the motor shaft 17.

In the embodiment shown by way of example, the housing of the blower head 9 runs between the coupling magnet 14 of the fan wheel 10 and the coupling magnet 16 of the motor shaft 17.

FIG. 4 schematically depicts one exemplary embodiment of a force-locking and/or interlocking connection as detachable coupling 11. The fan wheel 10 is, by way of example, connected to a fan shaft 18. Arranged at one end of the fan shaft 18 is a coupling element 19. The fan shaft 18 is, by way of example, mounted in the housing of the blower head 9 or the blower part 6 via the bearing 24. The bearing 24 is combined with a gasket 23 which is configured and arranged to prevent patient gas from reaching the drive device 12 from the blower head 9.

The motor shaft 17 has a coupling element 20 which is complementary to the coupling element 19 of the fan shaft 18. For example, an interlocking fit is achieved via the coupling elements 19, 20. Here, asymmetric or symmetric profiles of the coupling elements 19, 20 can be used. For simple assembly, guide elements can be additionally provided, along which, for example, the blower part 6 is guided. The guide elements then introduce the blower part 6 to the drive device 12 such that the two coupling elements 19, 20 interlock or mutually connect.

In some embodiments, as an alternative or in addition to the interlocking fit, a force fit, for example a friction fit, is also provided.

For example, the coupling elements 19, 20 can be pushed/pressed toward one another such that power transmission from drive device 12 or the motor shaft 17 to the fan wheel 10 or the fan shaft 18 is effected. For example, the coupling elements 19, 20 are flat for a force fit and/or have a conical shape. For example, the coupling element 19 is in the form of a hollow cone and the coupling element 20 is in the form of a cone which can be inserted into the hollow cone of the coupling element 19.

FIG. 5 schematically depicts a detail of an example ventilator. Besides the above-described removable blower part 6 and gas pass part 5, a separately removable motor part 21 is also provided in the exemplary embodiment shown. The motor part 21 comprises at least one motor or the drive device 12. The coupling 11 between drive device 12 and fan wheel 10 corresponds to an above-described detachable coupling 11, in the form of a force-locking and/or interlocking connection. By way of example, the coupling 11 is a magnetic coupling.

Supply of energy to the drive device 12 is, for example, achieved via inductive coupling between the energy source 22 and the drive device 12. As a result, the drive device 12 can, by of example, be arranged in an air-tight housing. Power transmission between drive device 12 and fan wheel 10 can, for example, likewise be effected magnetically. Alternatively or additionally, it is possible that the motor shaft 17 of the drive device 12 protrudes from the housing of the motor part 21 and is mounted in the housing wall of the motor part 21. Air-tight mounting is provided in the housing of the motor part 21, and so patient gas cannot reach the motor part 21, but at least cannot reach the drive device 12.

Such a modular design, in which for example different types and models of motor part 21, blower part 6 and gas pass part 5 are available, allows simple adaptation of the ventilator to the current need without having to keep multiple ventilators of different designs in reserve.

To sum up, the present invention provides:

1. A ventilator which comprises a blower head comprising at least one fan wheel and a housing having blower nozzles, and a drive device, the blower head together with the drive device being configured to convey a patient gas, and the blower head and the drive device being detachably coupled to one another via a coupling.
2. The ventilator of item 1, wherein the coupling is arranged and configured such that, in a region of the coupling, no patient gas reaches the drive device from the blower head.
3. The ventilator of at least one of the preceding items, wherein the coupling is a force-locking connection and/or an interlocking connection.
4. The ventilator of at least one of the preceding items, wherein the coupling between the drive device and the blower head is effected via at least two coupling elements.
5. The ventilator of at least one of the preceding items, wherein the drive device comprises a motor shaft, at least one first coupling element being arranged on the motor shaft.
6. The ventilator of at least one of the preceding items, wherein at least one second coupling element is arranged on the fan wheel and/or the fan wheel is connected to a fan shaft, the at least one second coupling element being arranged on the fan shaft.
7. The ventilator of at least one of the preceding items, wherein the coupling is a magnetic connection, the at least two coupling elements being in the form of at least two coupling magnets.
8. The ventilator of at least one of the preceding items, wherein at least one first coupling magnet is arranged on the fan wheel and at least one second coupling magnet is arranged on the motor shaft, the coupling magnets being arranged and configured to form a magnetic connection with one another.
9. The ventilator of at least one of the preceding items, wherein the housing of the blower head is at least partially arranged between the coupling magnet of the fan wheel and the coupling magnet of the motor shaft.
10. The ventilator of at least one of the preceding items, wherein the blower head is in the form of a wearing part or is in the form of a treatment part and is designed for treatment in a thermal disinfector and/or an autoclave.

11. The ventilator of at least one of the preceding items, wherein the coupling is a force-locking connection, the coupling between drive device and blower head being effected via a friction fit.
12. The ventilator of at least one of the preceding items, wherein the coupling is an interlocking connection, with the coupling elements having a symmetric coupling profile.
13. The ventilator of at least one of the preceding items, wherein the coupling is an interlocking connection, with the coupling elements having an asymmetric coupling profile.
14. A blower head which comprises at least one fan wheel and a housing having blower nozzles, the blower head being coupleable to a drive device of a ventilator of any of the preceding items via a detachable coupling.
15. A method for coupling a blower head comprising at least one fan wheel and a housing having blower nozzles to a drive device of a ventilator, wherein the method comprises using a detachable coupling for coupling the blower heat to the drive device.

LIST OF REFERENCE SIGNS

1 Expiration branch
2 Inspiration branch
3 Gas pass
4 Gas pass
5 Gas pass part
6 Blower part
7 Blower nozzle
8 Blower nozzle
9 Blower head
9*a* Housing
10 Fan wheel
11 Coupling
12 Drive device
13 Electrical connection
14 First coupling magnet
15 Bearing
16 Second coupling magnet
17 Motor shaft
18 Fan shaft
19 Second coupling element
20 First coupling element
21 Motor part
22 Energy source
23 Gasket
24 Bearing
100 Ventilator

What is claimed is:

1. A ventilator, wherein the ventilator comprises a blower head comprising at least one fan wheel connected to a fan shaft, a housing having blower nozzles, and a drive device having a motor shaft, the blower head and the drive device together being configured to convey a patient gas and being releasably couplable to one another via a coupling, the coupling comprising a first coupling element arranged on the fan shaft of the at least one fan wheel and a second coupling element that is complementary to the first coupling element arranged on the motor shaft of the drive device, the first and second coupling elements having a conical shape suitable for a force-fit connection in which the first and second coupling elements are pressed against each other such that force is transmitted from the motor shaft to the fan shaft.

2. The ventilator of claim 1, wherein the fan shaft is mounted in the housing by a bearing combined with a seal, the seal being configured to prevent patient gas from escaping from the blower head to the drive device.

3. The ventilator of claim 1, wherein the first coupling element is configured as a hollow cone and the second coupling element is configured as a cone that can be inserted into the hollow cone of the first coupling element.

4. The ventilator of claim 1, wherein the ventilator further comprises guide elements along which a blower part can be guided toward the drive device so that the first and second coupling elements can connect or engage with each other.

5. The ventilator of claim 1, wherein the blower head is in the form of a wearing part.

6. The ventilator of claim 1, wherein the blower head is in the form of a or treatment part which is configured to withstand treatment in a thermal disinfector and/or autoclave.

7. The ventilator of claim 1, wherein the first and second coupling elements have a symmetrical coupling profile.

8. The ventilator of claim 1, wherein the first and second coupling elements have an asymmetrical coupling profile.

9. A method for coupling a blower head of a ventilator that comprises at least one fan wheel and a housing having blower nozzles to a drive device of the ventilator, the blower head comprising at least one fan wheel connected to a fan shaft and the drive device being connected to a motor shaft, wherein the method comprises arranging a first coupling element on the fan shaft of the at least one fan wheel and arranging a second coupling element that is complementary to the first coupling element on the motor shaft of the drive device, the first and second coupling elements having a conical shape for a force-fit connection in which the first and second coupling elements are pressed against each other such that force is transmitted from the motor shaft to the fan shaft.

10. The method of claim 9, wherein the first coupling element is configured as a hollow cone and the second coupling element is configured as a cone that can be inserted into the hollow cone of the first coupling element.

11. The method of claim 9, wherein the first and second coupling elements have a symmetrical coupling profile.

12. The method of claim 9, wherein the first and second coupling elements have an asymmetrical coupling profile.

* * * * *